United States Patent
Loeb et al.

(10) Patent No.: US 6,740,107 B2
(45) Date of Patent: May 25, 2004

(54) DEVICE FOR TREATMENT OF ATRIOVENTRICULAR VALVE REGURGITATION

(75) Inventors: Marvin P. Loeb, Huntington Beach, CA (US); L. Dean Crawford, Irvine, CA (US); Randy P. Graham, Irvine, CA (US)

(73) Assignee: Trimedyne, Inc., Irvine, CA (US)

( * ) Notice: Subject to any disclaimer, the term of this patent is extended or adjusted under 35 U.S.C. 154(b) by 0 days.

(21) Appl. No.: 10/024,798

(22) Filed: Dec. 19, 2001

(65) Prior Publication Data
US 2003/0114901 A1 Jun. 19, 2003

(51) Int. Cl.[7] .............................................. A61B 18/22
(52) U.S. Cl. .............................. 607/89; 606/2; 606/13; 606/15; 607/90; 607/92; 607/101; 607/102
(58) Field of Search ..................... 607/89, 101, 102, 607/88, 90, 92; 606/2, 13, 15

(56) References Cited

U.S. PATENT DOCUMENTS

| | | | | |
|---|---|---|---|---|
| 4,777,951 A | * | 10/1988 | Cribier et al. ............. | 128/344 |
| 5,417,653 A | * | 5/1995 | Sahota et al. ................ | 604/20 |
| 5,607,421 A | * | 3/1997 | Jeevanandam et al. ....... | 606/15 |
| 5,730,741 A | * | 3/1998 | Horzewski et al. ............ | 606/1 |
| 5,921,982 A | * | 7/1999 | Lesh et al. .................... | 606/41 |
| 5,989,284 A | * | 11/1999 | Laufer .......................... | 607/96 |
| 6,102,886 A | * | 8/2000 | Lindquist et al. ............. | 604/22 |
| 6,224,566 B1 | * | 5/2001 | Loeb ............................ | 604/22 |

* cited by examiner

Primary Examiner—Linda C. M. Dvorak
Assistant Examiner—Aaron Roane
(74) Attorney, Agent, or Firm—Olson & Hierl, Ltd.

(57) ABSTRACT

A catheter device suitable for shrinking chordae tendineae of the human heart is provided having an energy conduit and a positioning device that facilitates the delivery of thermal energy, including coherent (laser) or non-coherent light, RF, microwave or ultrasound energy, to a predetermined region of the chordae tendineae or other collagen-containing tissue, such as the female urethra or the esophagus near the sphincter. The device comprises a tubular catheter containing an energy conduit, such as a fiber optic cable, adapted for delivering thermal energy to the tissue. The tubular catheter also contain a stabilizing device, disposed at its distal end, such as an asymmetrically shaped balloon or a retractable flexible metal hook. With the distal end of the catheter device positioned within a human heart, application of thermal energy to the chordae tendineae results in a shrinkage of the chordae, providing a treatment for primary mitral valve regurgitation.

17 Claims, 11 Drawing Sheets

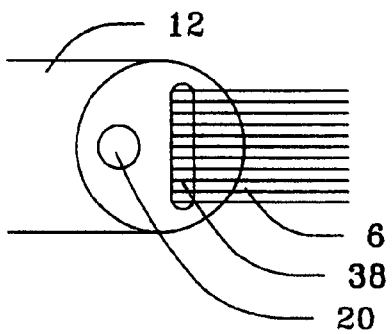
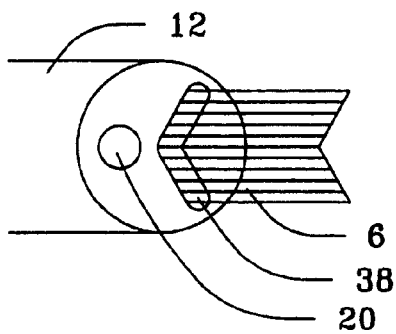
FIGURE 8     FIGURE 9
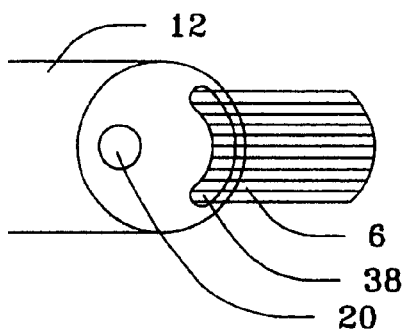
FIGURE 10
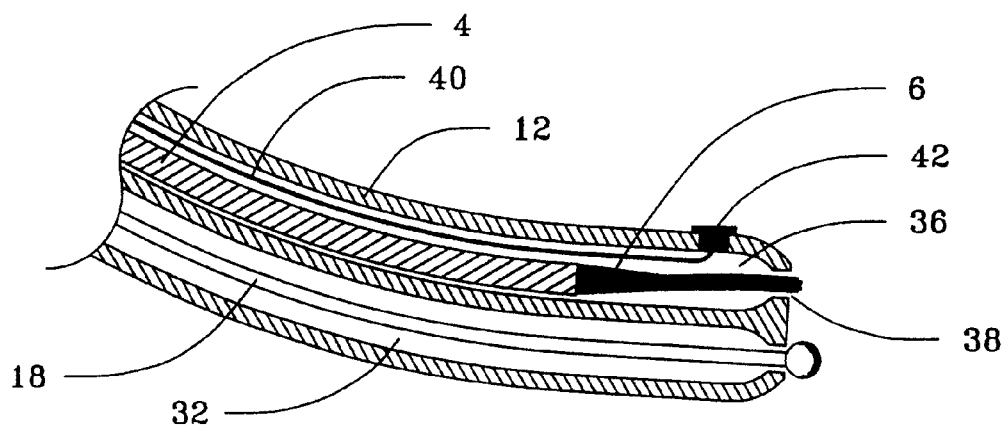
FIGURE 11

DEVICE FOR TREATMENT OF ATRIOVENTRICULAR VALVE REGURGITATION

FIELD OF THE INVENTION

The invention relates to devices for shrinking collagen in body tissue. More particularly, the invention relates to catheter devices for shrinking the chordae tendineae of the heart.

BACKGROUND OF THE INVENTION

The human heart consists of four muscular chambers: the right atrium, which connects to the right ventricle, and the left atrium, which connects to the left ventricle. The pumping action of the heart is achieved by contraction and relaxation of the heart muscles. The filling stage of the heart cycle is called diastole. The pumping stage is called systole. Both atria are filled at the same time during diastole and both ventricles expel their blood at the same time during systole.

During diastole, the heart chambers are at their largest volumes, and the atrioventricular valves, which separate the atria from the ventricles, are open. During systole, the heart muscles of the atria contract first, forcing their contents into the ventricles, and then, as the ventricles begin to contract, the increased ventricular pressure forces the atrioventricular valves to close, and the semilunar valves into the arteries to open, so that blood flows out of the heart and into the body tissues. Oxygen depleted blood is forced from the right ventricle into the lungs through the pulmonary artery, and oxygen rich blood is forced from the left ventricle into the remainder of the body through the aortic artery.

Each atrioventricular valve is composed of leaflets of connective tissue, called cusps, which are connected to the heart muscle tissue at the annulus of the aperture between the atrium and the ventricle. The unconnected portions of the cusps overlap with each other when the valves are in the closed position, such that the aperture between the chambers is completely closed. The cusps are stabilized and operated by roughly conical shaped muscles extending from the floor of the ventricles, called papillary muscles, which are connected to the cusps by fibrous, tendon-like structures called chordae tendineae (chordae). There is at least one papillary muscle for each cusp. The chordae begin at the apex of the cone of the papillary muscle and fan upward roughly to the periphery of the cusp. The chordae tendineae are the "guy wires" for the cusps of the atrioventricular valves. The mitral valve, between the left atrium and ventricle, has two cusps, while the tricuspid valve, between the right atrium and ventricle, has three cusps.

The pumping efficiency of the heart can be greatly diminished if the atrioventricular valves malfunction, allowing leakage of the blood from ventricle to atrium. A particularly common problem is weakening or stretching of the chordae, which condition allows the cusps of the affected atrioventricular valves to prolapse into the atrium during systole. Valve prolapse lowers the pumping efficiency of the heart by allowing a portion of the blood to flow in the wrong direction. Valve prolapse is particularly common with the mitral valve, a condition known as primary mitral valve regurgitation, but can also occur with the tricuspid valve. Other conditions which cause mitral valve malfunction include excessive lengthening or thickening of the cusps and the annulus of the valve becoming stretched or loose. Malfunction of the mitral valve occurs in an estimated 1.4% of the population and can lead to a variety of problems, including weakness, persistent nausea, atrial or ventricular fibrillation, a greater risk of infective endocarditis, congestive heart failure, and increased risk of sudden death.

Co-owned U.S. Pat. No. 5,989,284 to Laufer discloses a method of treating primary mitral value regurgitation by applying thermal energy to shorten the chordae. The method of Laufer involves insertion of a catheter into the ventricle of the heart, and placing the tip of the catheter in contact with the chordae. Shortening of the chordae can prevent prolapse of the atrioventricular valve cusps.

The chordae of the human heart are composed predominantly of tightly coiled strands of collagen. Application of heat to the chordae, raising the temperature of the tissue to about 50–55° C., causes the collagen strands to uncoil and straighten. Upon cooling the collagen resumes its tightly coiled shape, however, the collagen strands tend to entangle with one another, causing the total volume of the collagen, and thus the chordae, to shrink. Shrinkage of the chordae can be an effective treatment of primary mitral regurgitation and the related problem of tricuspid valve regurgitation. Likewise, heating the cusps or the annulus, which also contain collagen, to about 50–55° C., causes the collagen therein and the cusps or annulus to shrink in size and length.

The present invention provides catheter devices for shrinkage of tissue, such as the chordae, cusps or annulus of valves of the human heart and other tissues, such as the esophagus in the area of the sphincter or the female urethra below the bladder. Heat is applied to the target tissue via a heat transfer means on the catheter tip. The method of Laufer is a minimally invasive means of treating mitral regurgitation, however, appropriate placement of the catheter tip, and keeping it in place can be difficult, particularly in a moving organ, such as the heart.

In some applications, it is possible to visualize the tissue during laser treatment by means of an endoscope. This is not possible in a beating heart, due to the opaque nature of blood. In addition, the chordae are difficult to visualize by ultrasonic or x-ray techniques, thus, application of energy to the chordae, as in the method of Laufer, must be performed "blind." A similar problem exists in treatments of female stress incontinence (FSI) involving thermal shrinkage of the tissue surrounding the urethra below the bladder. The small diameter of the urethra (about 1.5 to 5 millimeters) makes endoscopic viewing difficult. It would also be beneficial to shrink tissues such as the esophagus in the area of the sphincter to treat gastro-esophageal reflux disease (GERD).

It would be desirable to be able to shrink the chordae tendineae of the heart and other tissues in a minimally invasive, non-surgical catheterization procedure that would allow precise and stable placement and application of energy to the tissues. It would also be desirable to provide a treatment that could be rendered in a few minutes in a hospital cardiac catheterization laboratory or outpatient department or an outpatient surgical center, with little recuperation time.

SUMMARY OF THE INVENTION

A catheter device suitable for shrinking chordae tendineae of the human heart is provided with an energy conduit (e.g., an optical fiber, electrical conducting cable, or other similar energy transmitting device) and a positioner device that facilitates the delivery of thermal energy to a predetermined region of the chordae tendineae.

In a preferred embodiment, a catheter containing an optical fiber, having a distal end portion encompassing a directional energy emitting device within an asymmetrically-shaped balloon, positions the energy conduit and directionally delivers energy to tissues. The asymmetric shape of the balloon allows an operator to precisely determine the orientation of the device within the tissue using ultrasound or x-ray imaging, for example. The distal end of the catheter is closed and has a blunt shape. The distal end portion of the catheter within the balloon contains an aperture that admits inflation fluid into the balloon, and directs the energy emission from optical fiber through only one portion of the asymmetric balloon. Thus, by imaging the inflated balloon within the tissue, the operator can determine the direction of laser energy emission.

In another embodiment of the present invention a fiber optic cable or other thermal energy delivery device is contained within a tubular sheath that is open at its distal end, such that laser or other thermal energy can be emitted by the cable through the distal opening of the sheath. Also present within the sheath is a flexible metal positioner and stabilizer rod, having a hook-shaped distal end portion and a blunt, atraumatic distal end. The blunt end of the flexible metal positioner and stabilizer rod can be in the form of a ball or other similar form, which will tend to slide off, rather than penetrate tissue when the end of the rod comes into contact with the tissue.

The hooked distal end portion of the rod is helicoid, i.e., having a configuration that approximates that of a helical coil. The length of the distal end portion is approximately 3 to 6 times the radius of curvature of the coil, i.e., the end portion comprises roughly one half to one loop of the helical coil. Both the cable and the rod are independently slidably moveable within the sheath. The distal end of the fiber optic cable can be retracted into or extended out of the distal opening of the sheath, and, independent of the cable, the hooked distal end portion of the flexible rod can be withdrawn into the sheath or extended therefrom.

The flexible metal rod can be preferably composed of a superelastic shape-memory alloy such as nitinol, which has been previously formed into its hooked shape by bending the distal end portion of the rod into a helical-coil shape and heat-treating the bent portion of the rod at a temperature of about 300° C. to 800° C. to fix the shape. When the distal end portion of the rod is retained within the sheath, the end portion of the rod straightens due to pressure from the relatively more rigid sheath. When substantially extended from the distal opening of the sheath, the flexible rod returns to its helical-coil/hooked shape. The distal end portion of the rod can be repeatedly coiled and uncoiled by extending the end portion out of or into the sheath, respectively, due to the shape-memory properties of the superelastic alloy.

The sheath portion of the catheter device defines one or more lumens in which the energy conducting cable and flexible rod are disposed. In a preferred embodiment of the invention, the flexible sheath defines two lumens, the energy conducting cable being situated in a first lumen and the flexible rod being situated in a second lumen. In addition, there can be other lumens within the sheath, for example, there can a lumen for a guide wire, commonly used to position a catheter within a specific area of the anatomy, or a lumen for delivery to, or withdrawal of fluids from, the irradiation site. Alternatively, the catheter device of the present invention can have a sheath with a single lumen, wherein the rod and cable are positioned side by side in the same lumen, through which fluid can also be infused or withdrawn.

The proximal end of the flexible sheath can be attached to a handpiece to provide the operator of the device a method of controlling the position and orientation of the device. The handpiece can include a mechanism or mechanisms for manipulating either the flexible rod, the energy cable, the sheath or any combination thereof.

The energy conducting cable extends throughout the whole length of the device, generally exiting the device at the proximal end of the handpiece and extending further to a coupler at the proximal end of the cable, adapted for connection to an energy source. When the energy source is a laser generator, the coupler is an optical coupler, and the cable comprises at least one, and preferably several optical fibers. A plurality of optical fibers can be bound together in a sleeve or wrapped in a plastic film, such as shrink-wrap, to protect the fibers and create a single optical cable.

Alternatively, the cable can comprise one or more insulated wires, adapted at their proximal end for connection to an electrical power or radiofrequency (RF) energy source. The distal end of each wire, located in close proximity to the distal opening of the sheath, is adapted for connection to a variety of energy emitting devices, such as electrical resistive heating loops, ultrasonic generators, microwave generators, RF electrodes, and the like. The individual wires are preferably bound together as described for the optical cable above.

Optionally, a slidable control button or lever, which can be engaged by the operator's thumb, is disposed within a slide channel on the exterior of the handpiece. The portion of the button which extends through the slide is attached to a metal sleeve which, in turn, is attached to and surrounds the energy conducting cable. When the button is advanced a predetermined distance, an audible "click" can be created by an optional ratchet mechanism, and the energy cable is extended a like distance out of the distal end of the sheath in which it is disposed. A similar mechanism can be used to control the extension and retraction of the flexible metal rod to deploy the hooked distal end of the rod or to manipulate the position of the sheath relative to the energy cable or rod. Alternatively, the rod, sheath and/or energy cable can be manipulated by a rotatable knob attached to a shaft, which shaft is operably attached to the energy cable, the sheath, or the rod in a manner such that the cable, rod or sheath can be slidably moved distally or proximally by turning the knob. In an alternative embodiment, the operator can optionally deploy the flexible metal rod or cable by grasping the proximal end of the rod or cable and manually sliding the rod or cable forward or backward a predetermined distance.

In use, an operator positions the distal end of the sheath within a ventricle of the heart, in close proximity to a papillary muscle, with both the distal end portion of the rod and the distal end of the cable substantially retracted into the sheath. The operator can guide the device into its desired position by inserting it over an earlier placed guide wire, can thread the device through a tubular catheter that has been pre-positioned in the heart, by articulating the distal end portion of the sheath or by any other acceptable method known in the medical art. After proper positioning, the distal end portion of the rod is then slid forward to gradually extend the end portion of the rod from the distal end of the sheath. As the distal end portion of the rod becomes less constrained, it gradually resumes its curved shape, and can thus encircle the papillary muscle and then be manipulated up to encircle the chordae tendineae that are attached to the papillary muscle.

After the rod has encircled the chordae, the operator extends the distal end of the energy cable out of the distal opening of the sheath, placing the distal end of the cable in close proximity to, or in contact with the chordae. The hooked end of the rod acts as a stabilizer for the distal end of the catheter device. Thermal energy, in the form of coherent light (laser), ultrasound, microwave, RF energy, or heat generated from an electrical resistive heating coil is supplied to the chordae, by the energy cable, in a quantity sufficient to raise the temperature of the collagen in the chordae to about 50 to 55° C., causing the collagen strands to uncoil. When the emission of energy is ceased, the chordae shrink upon cooling of the collagen, thus tightening the chordae and preventing further prolapse. After the thermal irradiation of the chordae has ceased, the rod and cable can be withdrawn fully, or partially into the sheath, and the catheter device can be repositioned above or below the first treated area of the chordae for further treatment or removed entirely.

In a preferred embodiment, the distal end of the cable can be encased in an asymmetric, energy-transmissive balloon attached to the distal end of a catheter. For treatment of atrioventricular valve malfunction, such as primary mitral valve regurgitation, the balloon-tipped catheter device can be moved, with the balloon deflated, into position within the left ventricle using either a conventional guide wire or a guiding catheter, which has been previously inserted into an artery, such as the femoral artery, and advanced through the aorta and the aortic valve into the left ventricle, as is known in the art. The distal end portion of the asymmetric balloon-tipped catheter can be formed into a fixed angle, or the catheter can contain a control element for changing the angle of the distal end portion of the catheter to facilitate precise placement of the asymmetric balloon near or in contact with the chordae.

Likewise, the distal end portion of the device can be positioned near or in contact with the cusps or the annulus of the valve, and the procedure can be carried-out, as described above, to shrink the same.

An optical fiber extends throughout the length of the catheter and is adapted at its proximal end for connection to a source of laser light. The distal end of the optical fiber is positioned opposite the aperture in the distal end portion of the catheter, so that laser light emission from the optical fiber is directed out of an aperture at an angle in the range of about 60 to about 100 degrees from the axis of the fiber. The balloon surrounding the distal end portion of the catheter is asymmetric in shape, having the side of the balloon facing the aperture extending further from the catheter than the opposite side of the balloon. When the balloon is inflated with a fluid that appears opaque under ultrasound or x-ray imaging, the orientation of the balloon within the heart chamber is readily determined. Thus, an image showing the orientation of the greater inflated side of the balloon also indicates the direction of energy emission to the operator.

The balloon catheter can encompass lumens for acceptance of a guide wire, and/or a hooked stabilizing rod such as is described hereinabove. The catheter can also include thermocouples to measure the temperature of the tissue being irradiated and/or the inflation fluid within the balloon.

The proximal end of the balloon catheter preferably comprises a handpiece adapted for delivering inflation fluid through the catheter and into the balloon through the aperture in the distal end portion of the catheter The handpiece can also contain a mechanism for controlling the angle of the distal end portion of the catheter for more precise positioning of the balloon within the tissue.

BRIEF DESCRIPTION OF THE DRAWINGS

In the drawings.

FIG. 8 is a partial, expanded view of the distal end of a preferred embodiment of the device of FIG. 6 with the blunt end of the flexible metal rod positioned just distal to the opening of the second lumen and with the opening of the first lumen having a substantially linear, slit-like shape, such that the end portions of the individual optical fibers form a substantially linear, brush-like array when they are extended out of the distal opening of the first lumen;

FIG. 9 is a partial, expanded view of the distal end of a preferred embodiment of the device of FIG. 6 with the blunt end of the flexible metal rod positioned just distal to the opening of the second lumen and with the opening of the first lumen having a substantially V-shape, such that the end portions of the individual optical fibers form a substantially V-shaped array when they are extended out of the distal opening of the first lumen;

FIG. 10 is a partial, expanded view of the distal end of a preferred embodiment of the device of FIG. 6 with the blunt end of the flexible metal rod positioned just distal to the opening of the second lumen and with the opening of the first lumen having a substantially curved slit-shape, such that the end portions of the individual optical fibers form a substantially curved array when they are extended out of the distal opening of the first lumen;

FIG. 11 is a partial, cross-sectional view of the distal end of a preferred embodiment of the device of FIG. 6 having a control wire attached to the fiber optic cable, which allows the operator to slide the fiber optic cable distally and proximally within the first lumen of the sheath in order to project the optical fibers in the end portion of the cable through the distal opening of the lumen;

DETAILED DESCRIPTION OF PREFERRED EMBODIMENTS

Figure 1:
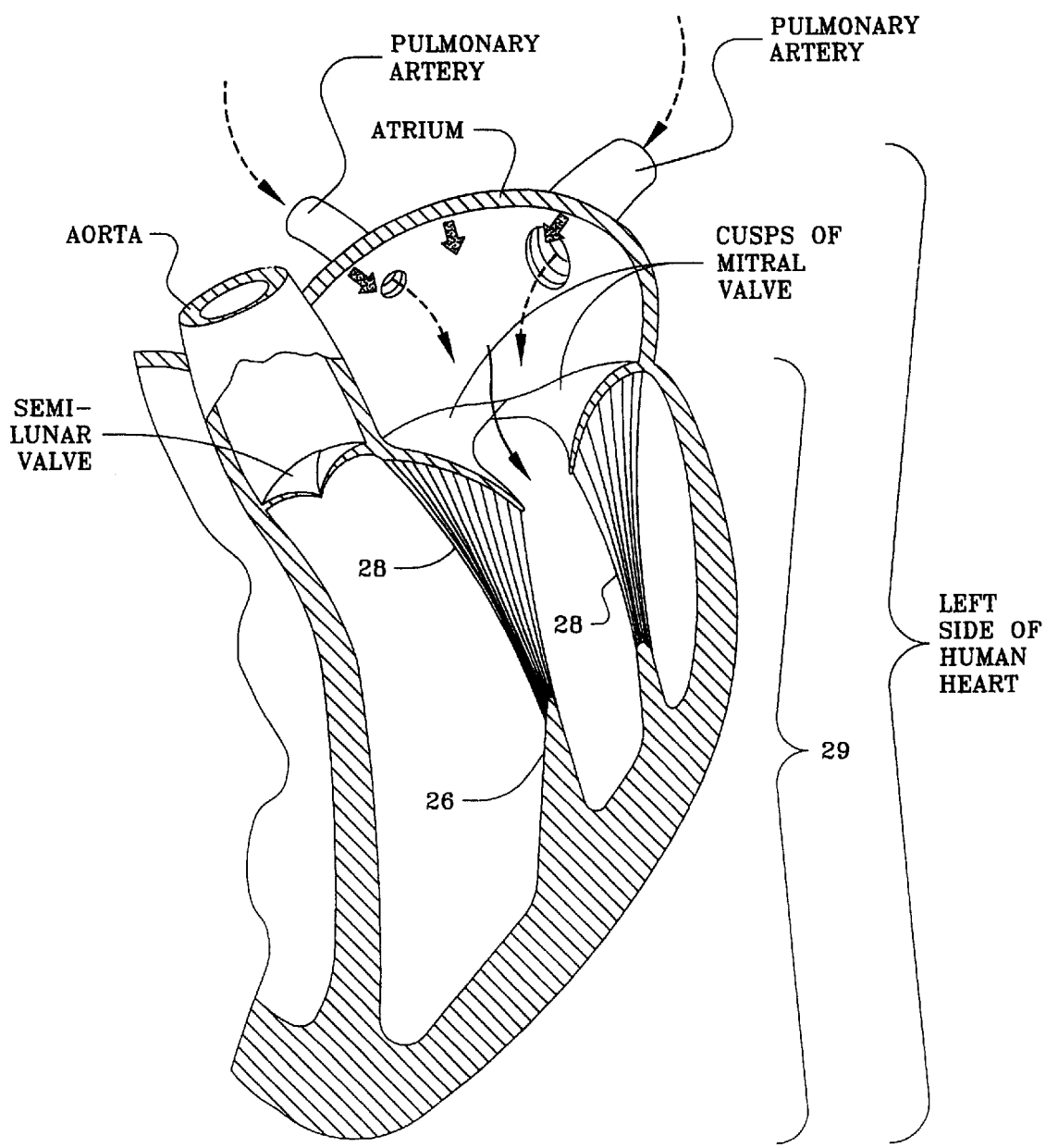
FIG. 1 is a schematic of the human heart illustrating the position and morphology of the atrioventricular valves, the chordae tendineae and the papillary muscles.

While this invention is susceptible of embodiment in many different forms, there are shown in the drawings and will be described in detail herein specific embodiments thereof, with the understanding that the present disclosure is to be considered as an exemplification of the principles of the invention and is not to be limited to the specific embodiments illustrated.

FIG. 1 depicts the anatomy of the human heart, illustrating the relative size and orientation of the chordae, papillary muscles and atrioventricular valves. As shown in FIG. 1, the chordae rise in a roughly conical array from the papillary muscles up to the periphery of the cusps of the atrioventricular valves.

Figure 2:
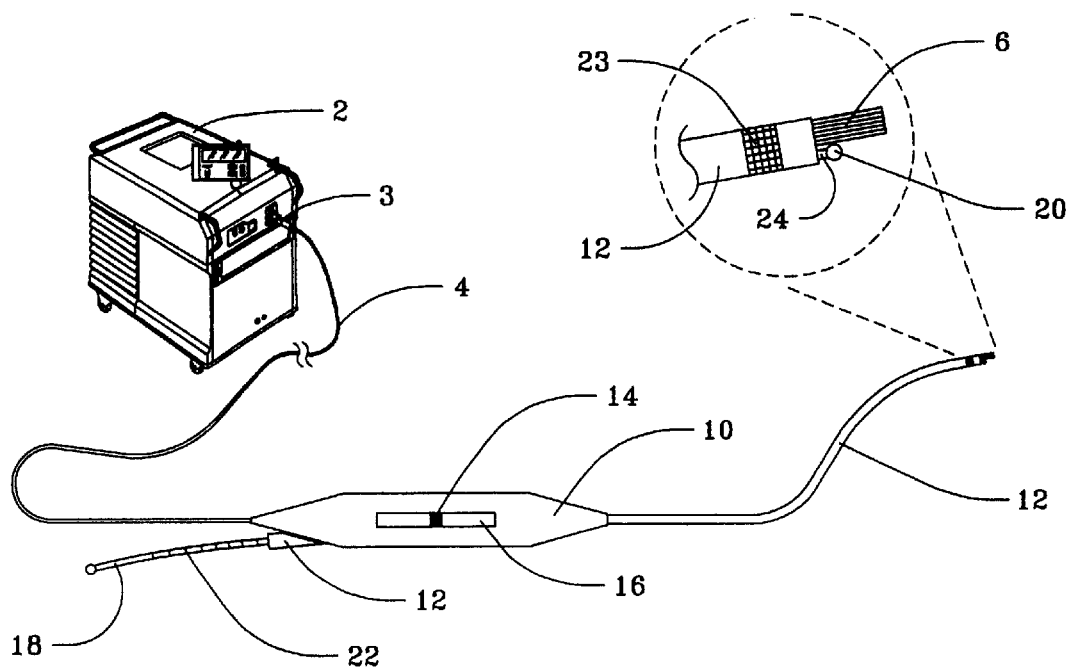
FIG. 2 is a schematic external view of a preferred embodiment of the catheter device of the present invention, operably connected to an energy source such as a laser energy or electrical current source.

As shown in FIG. 2, a source of light energy 2, such as a laser or high energy light source, is optically coupled through an optical connector 3 to an energy conducting cable 4, which is a fiber optic cable composed of a plurality of optical fibers 6. Cable 4 extends through handpiece 10 and flexible sheath 12, and is moveable therein. Control button 14 is moveably disposed within slide channel 16 in handpiece 10, and can be extended and retracted by thumb pressure of the operator (not shown). Control button 14 extends through channel 16 and is attached to cable 4 by an adhesive or similar expedient. A ratchet mechanism (not shown) that emits an audible "click" each time control button 14 is advanced a given distance, for example, one millimeter, can be provided, if desired.

Sheath 12 comprises at least one lumen in which a flexible metal rod 18 and cable 4 are enclosed. Optionally, the sheath 12 can define two or more lumens, with flexible metal rod 18 enclosed in one lumen and cable 4 enclosed in another lumen. The sheath 12 can also define additional lumens, for example, a lumen for acceptance of a guide wire to facilitate placement of the device within the body, as is known in the art, or a lumen for withdrawal of fluids from, or infusion of fluids into the tissue site. The distal end portion 24 (FIG. 4) of rod 18 has a permanently hooked shape, but is elastic enough to temporarily straighten when constrained within sheath 12, as shown in FIG. 2.

Rod 18 extends through handpiece 10 and sheath 12, and terminates at its distal end in a blunt, roughly spherical ball 20, or any other atraumatically-shaped structure that will resist penetration of body tissues e.g., a rounded or blunt shape. Rod 18 is slidably moveable within the sheath 12, such that a hook-shaped distal end portion of the rod (not shown) can be extended out of the distal opening of the sheath 12. The proximal end portion of rod 18 can have markings 22 that allow an operator to determine the distance that the hooked distal end portion of rod 18 has been deployed from the distal opening of sheath 12.

The flexible metal rod 18 is preferably composed of a superelastic shape memory alloy such as nitinol. The distal end portion of the rod has been preformed into a hook-shape by bending the rod into the desired shape and heat treating the bent portion at a temperature of from about 300° C. to about 800° C. for a time sufficient to fix the shape. Nitinol is a substantially 1:1 alloy of nickel and titanium. Nitinol generally has an atomic ratio of nickel to titanium in the range of about 49:51 to about 51:49. Nitinol alloys can also comprise about 0.1 to about 5% by weight of other elements such as iron, chromium and copper.

The distal end of sheath 12 can include a band of ultrasound-opaque and/or radio-opaque material 23, to enable an operator to precisely determine the position of the distal end of the device when it is deployed within a patient's body using x-ray (fluoroscopic) imaging, ultrasound imaging (preferably a transesophageal echo (TEE) imaging system) or a catheter-borne ultrasound imaging device. A preferred catheter-borne ultrasound device is the AcuNav® catheter made by Accuson, Inc. of Mountain View, Calif., which is generally deployed in the right ventricle to transseptally view the left ventricle and the papillary muscles, chordae, cusps and annulus of the mitral valve. The proximal end of flexible sheath 12 is attached to the distal end of handpiece 10 in any convenient manner, such as by an adhesive.

In an alternative embodiment of the device of FIG. 2, laser light source 2 can be replaced by an electrical current source and the energy conducting cable 4 is a wire cable comprising at least one electrically conductive, insulated wire (not shown). The cable 4 is adapted at its proximal end for connection to the electric current source 2 and the distal end portion of the cable comprises an energy emission source such as a radio frequency (RF) electrode, resistive heating loop, ultrasound generator, or microwave energy generator. The energy emission source 2 is operably connected to the cable 4 such that upon application of electric current to cable 4, the energy emission source 2 is capable of delivering thermal energy to a tissue site.

Figure 3:
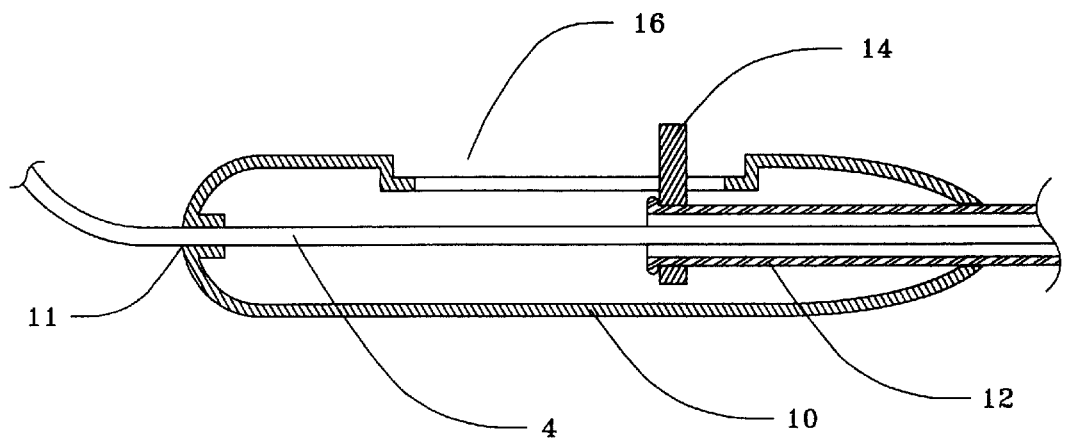
FIG. 3 is a cross-sectional detail of the handpiece of an embodiment of the device of FIG. 2 showing a mechanism for moving the flexible sheath relative to the energy conducting cable.

FIG. 3 provides a partial cross-sectional view of one embodiment of handpiece 10 of the device of FIG. 2, wherein button 14 is attached to sheath 12 and provides a means of moving sheath 12 relative to energy conducting cable 4, thus allowing the operator to expose or cover the distal end portion of cable 4 by pulling the button proximally or pushing the button distally, respectively. In this embodiment, the energy conducting cable 4 is fixedly attached to handpiece 10 at juncture 11 by an adhesive or other expedient. As seen in FIG. 3, sheath 12 can be moved relative to handpiece 10 by sliding button 14 which is attached to sheath 12 by an extension (not shown). Button 14 is disposed within a longitudinal channel 16 in handpiece 10. When button 14 is advanced or withdrawn, an optional ratchet mechanism (not shown) emits an audible "click". One audible "click" made by the ratchet mechanism can indicate that energy cable 4 has been advanced a chosen distance, for example 1 millimeter. Optionally, an indicator arrow on button 14 (not shown) can indicate the distance energy cable 4 has been advanced from the distal end of the sheath 12 by means of a distance scale along the length of channel 16 (not shown).

An alternative embodiment of the device of FIG. 3, not shown, has the button 14 fixedly attached to the energy conducting cable 4. In this embodiment, cable 4 is freely moveable through handpiece 10 and sheath 12, and sheath 12 is fixedly attached to handpiece 10. When button 14 is moved forward in channel 16, cable 4 is slid forward relative to sleeve 12, thus affording a way of extending the distal end of cable 4 (not shown) out of the distal opening of sheath 12.

Figure 4:
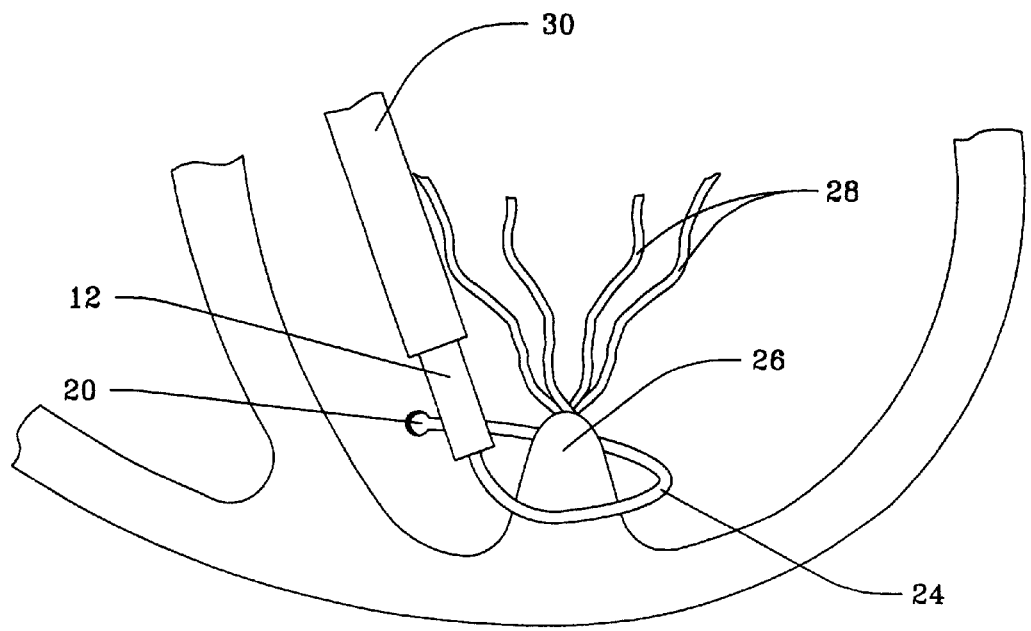
FIG. 4 is an external view of the distal end portion of the device of FIG. 2, shown with the hooked distal end portion of the flexible metal rod encircling a papillary muscle within a ventricle of a human heart.

FIG. 4 is a cross-sectional view of the lower portion of the left ventricle of a human heart and a portion of the distal end of the device of FIG. 2 oriented as it would be in use, just prior to final placement for thermal treatment of the chordae. As shown in FIG. 4, the hook-shaped distal end portion 24, of flexible metal rod 18, is positioned around a papillary muscle 26, below the chordae 28. The distal end portion 24 of rod 18 is deployed by an operator (not shown) by sliding the rod 18 distally relative to sheath 12, after the distal end of the device has been properly positioned by the operator.

The device of FIG. 4 can be positioned in the heart by threading it through a conventional catheter 30, which has been previously placed in proper orientation within the ventricle by methods well known in the art. The precise position and orientation of the distal end of the device can be determined by ultrasonic or x-ray imaging, if desired. The distal end portion 24 of rod 18 has a roughly helicoid, hooked shape. Distal end portion 24 of rod 18 has a radius of curvature of about 2.5 millimeters to about 30 millimeters, preferably about 5 to 15 millimeters, when unconstrained by sheath 12. The length of distal end portion 24 of rod 18 is generally about 3 to about 6 times the radius of curvature, i.e., the end portion comprises roughly about one half loop to about one loop of a helical-coil.

Figure 5:
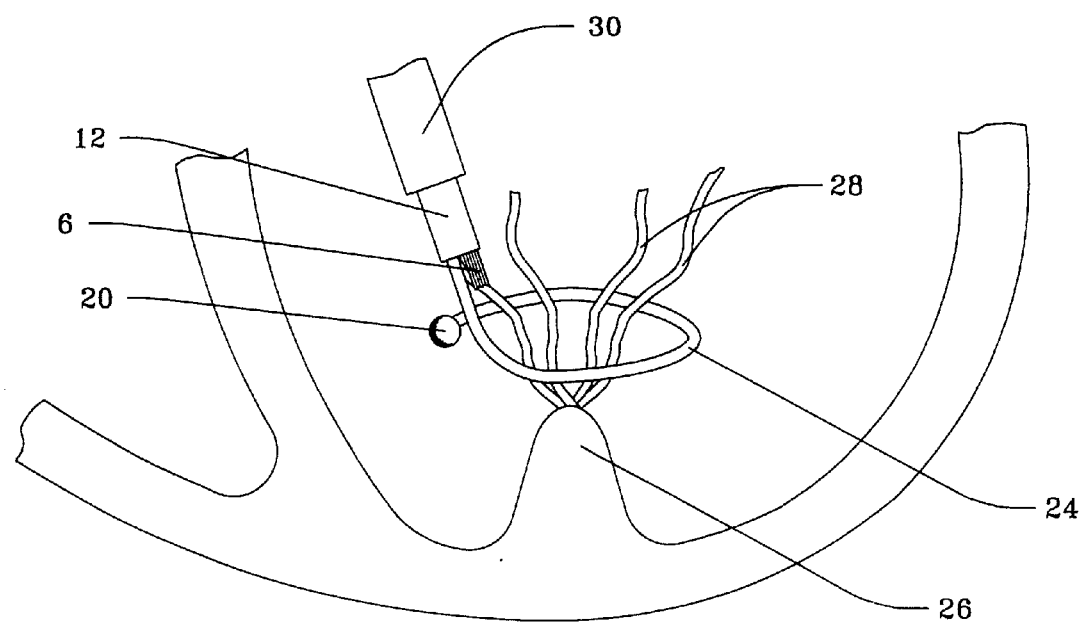
FIG. 5 is an external view of the distal end portion of the device of FIG. 2, shown with the hooked distal end portion of the flexible metal rod encircling chordae within a ventricle of a human heart, and with the distal end portion of the energy conducting cable extended out of the distal opening of the flexible sheath, and in close proximity to the chordae.

FIG. 5 illustrates the deployment of the hooked end portion 24 of rod 18 over the chordae 28, by withdrawing sheath 12 partially into catheter 30. As shown, optical fibers 6 of optical cable 4 have been extended out from the distal opening of sheath 12.

In FIG. 5, the distal ends of the optical fibers 6 are positioned in close proximity to, or in contact with the chordae 28, such that the chordae 28 can be precisely heated by irradiation with laser light from optical fibers 6. After irradiation, optical fibers 6 can be withdrawn back into sheath 12, and the hooked end portion 24 of rod 18 can be withdrawn into sheath 12, so that the device can be removed from the patient through catheter 30 or can be repositioned for another treatment above or below the area first treated. Rod 18 is composed of a superelastic shape memory alloy so that it is flexible, and the curved end portion 24 is sufficiently rigid and capable of substantially straightening rod 18 when it is slid proximally, relative to sheath 12 by the operator (not shown), to draw the end portion 24 of rod 18 back into the sheath 12.

Figure 6:
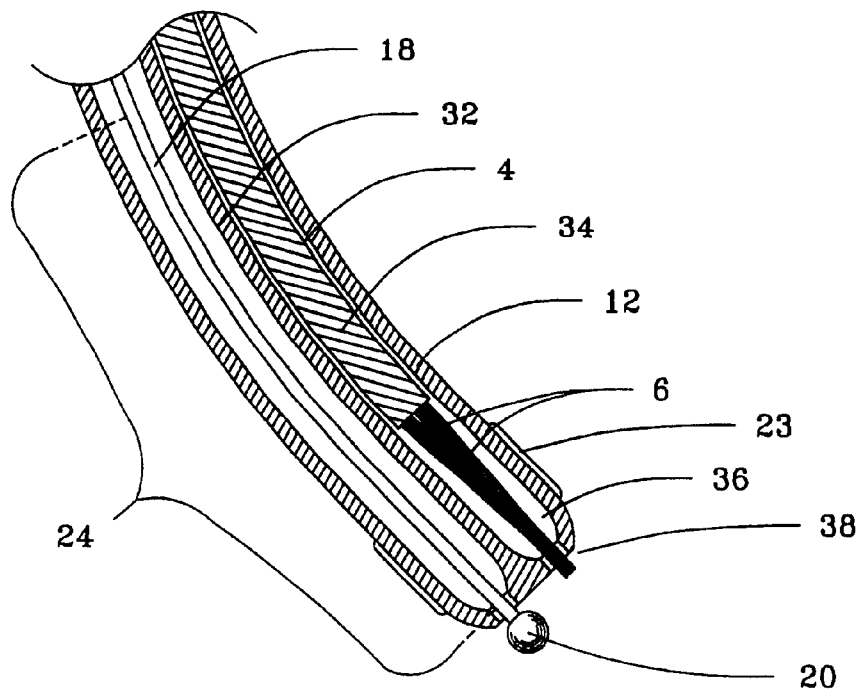
FIG. 6 is a partial cross-sectional end view of a dual lumen embodiment of the catheter device showing a fiber optic cable in a first lumen and a flexible metal rod in the second lumen.
Figure 7:
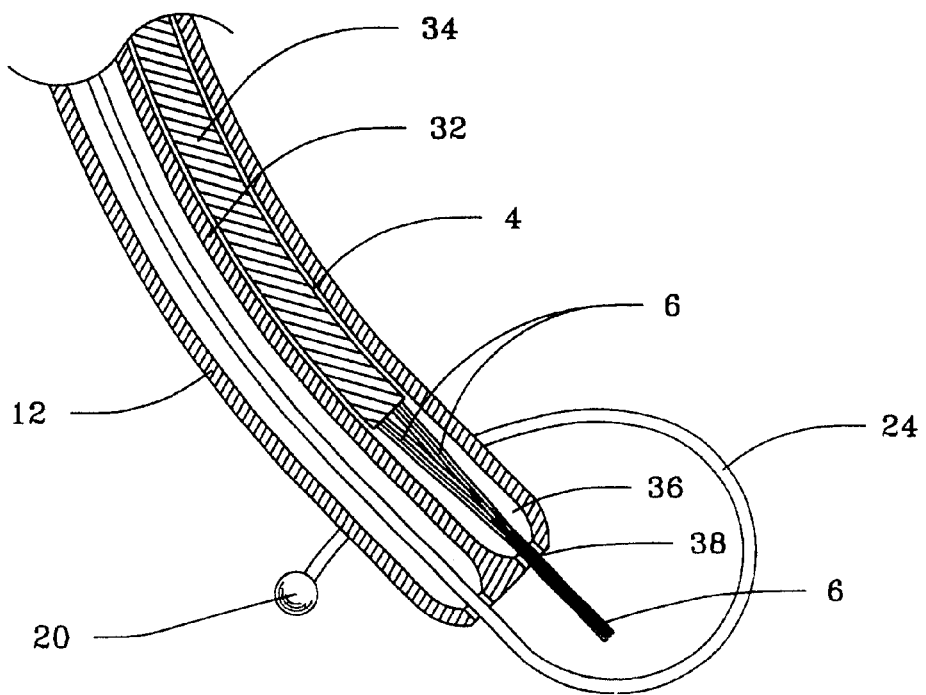
FIG. 7 is a partial cross-sectional view of the device of FIG. 6 showing the distal end portions of the optical fibers extended out of the distal opening of the first lumen and the hooked end portion of the flexible metal rod deployed outside of the distal opening of the second lumen.

A partial cross-sectional view of a dual-lumen embodiment of the present invention is illustrated in FIGS. 6 and 7. In FIG. 6, flexible metal rod 18 is contained within a first lumen 32 of sheath 12. In this illustration, the curved end portion 24 of rod 18 is substantially disposed within the relatively more rigid lumen 32 so that the end portion 24 of rod 18 becomes substantially straightened by the sheath, relative to its unconstrained hook-shape. Fiber optic cable 4, comprising a plurality of optical fibers 6, bound together by a casing 34, is disposed within a second lumen 36 of sheath 12. Casing 34 covers all but the distal end portions of optical fibers 6. Optical fibers 6 can be projected out from distal opening 38 of lumen 36 to a distance in the range of about 3 millimeters to about 25 millimeters, preferably about 6 to about 15 millimeters.

In FIG. 7, the distal end portion 24 of rod 18 is shown in its unconstrained curved-shape, after being pushed out of lumen 32 of sheath 12 by an operator (not shown). In like manner, optical fibers 6 are shown deployed through opening 38 of lumen 36, as they would be during irradiation of the chordae.

The distal opening 38 of lumen 36 can have any desired configuration, however, several configurations are preferred. FIGS. 8, 9, and 10 illustrate three alternative preferred configurations of distal opening 38 of lumen 36. As shown in FIG. 8, opening 38 can have a substantially linear configuration, so that optical fibers 6 form a linear, brush-like array when the fibers are advanced distally through the opening by the operator. FIG. 9 illustrates a substantially V-shaped opening 38, such that the optical fibers 6 form a roughly V-shaped array when pushed through the opening by the operator. FIG. 10 shows a curved form of opening 38.

A partial cross-sectional view of the distal end portion of a preferred embodiment of the dual lumen device of FIG. 6 is shown in FIG. 11. Control wire 40 is fixedly attached near the distal end of catheter 12 by metal cleat 42, or other expedient. Control wire 40 allows an operator to articulate the distal end portion of catheter 12 into a desired curved shape. FIG. 11 shows the distal end portions of optical fibers 6 substantially retracted into lumen 36 of catheter 12. Control wire 40 can be made of stainless steel or a superelastic alloy such as nitinol, preferably with a diameter of about 0.005 inches to about 0.010 inches.

Figure 12:
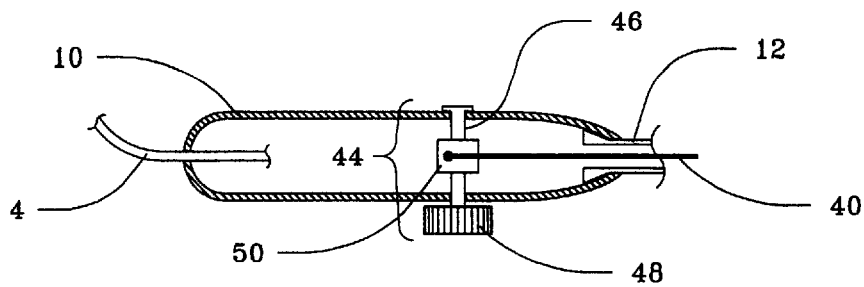
FIG. 12 is a cross sectional detail of a preferred embodiment of a handpiece useful in combination with the device of FIG. 11 having a reel mechanism for moving a control wire.

A preferred embodiment of the handpiece of dual lumen device of FIG. 11, shown in FIG. 12, has a reel mechanism 44 for moving control wire 40. For clarity, optical cable 4 is not shown within the handpiece 10. Reel 44 comprises a rotatable shaft 46, extending substantially through handpiece 10, and pivotally moveable therein, having at least one end projecting above the outer surface of handpiece 10. Knob 48 is axially attached to the end of shaft 46 that projects above the outer surface of the handpiece 10. The proximal end of control wire 40 is attached to shaft 46 at a point 50, such that when an operator turns knob 48, control wire 40 is wound around shaft 46, thus pulling control wire 40 and causing the distal end portion of catheter 12 to be formed into a curved shape of a desired arc or angle. In this embodiment, control wire 40, when in a completely unwound state, would return sheath 12 to its original, substantially straight shape. Alternatively, a second control wire (not shown), could be attached near the distal end of catheter 12 on the side opposite control wire 40, so when knob 48 is turned to extend control wire 40, the second control wire (not shown) is retracted to mechanically straighten catheter 12 by opposing the force exerted by wire 40, as known in the art.

Figure 13:
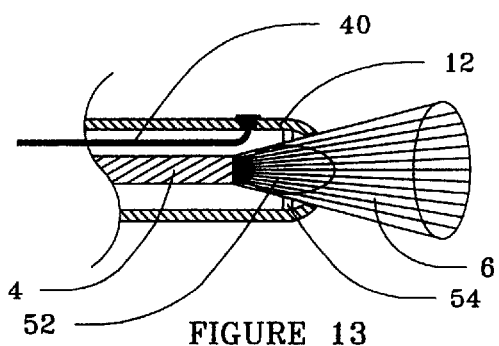
FIG. 13 is a cross sectional detail of a preferred embodiment of the first lumen of the device of FIG. 11 having an obturator mechanism for spreading the optical fibers of the distal end portion of the optical cable into a roughly conical array when the cable is slid distally within the lumen to project the fibers out of the distal opening of the lumen.

As shown in FIG. 13, the distal opening 38 of lumen 36 can contain an obturator device 52 that partially closes the opening and forces the distal end portions of optical fibers 6 to exit lumen 36 along the periphery of opening 38 to form a roughly conical array when cable 4 is moved distally relative to opening 38 of lumen 36. Obturator 52 can be attached to the periphery of opening 38 by struts 54. Obturator 52 can have a roughly football shape as illustrated in FIG. 13 or can be spherical, conical, pyramidal, or any other useful configuration.

Figure 14:
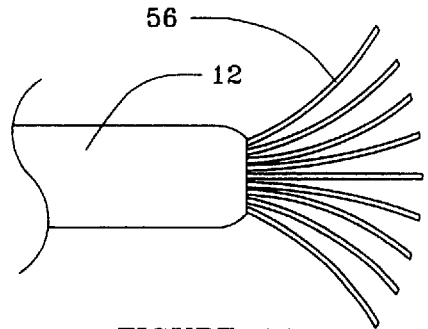
FIG. 14 is a partial external view of an alternative preferred embodiment of the first lumen of the device of FIG. 11 wherein the end portions of the optical fibers of the fiber optic cable are encased in curved flexible metal tubes, which cause the fibers to spread into a fan-like array when the end portions of the fibers are projecting out of the distal opening of the first lumen.
Figure 15:
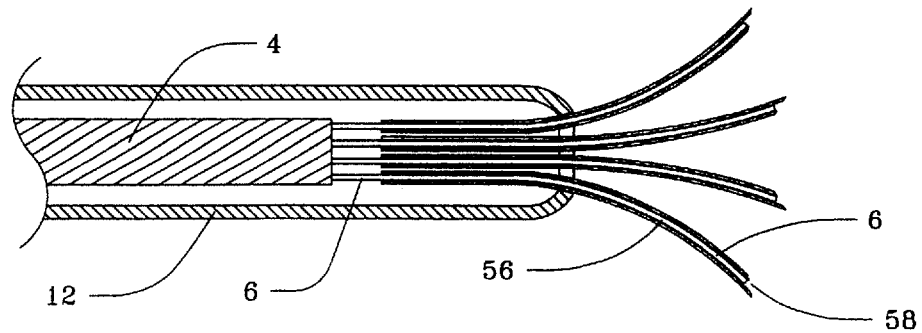
FIG. 15 is a partial, cross-sectional view of the device of FIG. 14, illustrating the disposition of the flexible metal tubes over the end portions of the optical fibers.

FIGS. 14 and 15 present partial views of another preferred embodiment of the device of FIG. 6, wherein the distal end portions of optical fibers 6 are encased in curved flexible metal tubes 56, open at their distal ends to allow laser light to be emitted from optical fibers 6 disposed therein. For purposes of clarity, the first lumen, containing the flexible metal rod, is not shown. Tubes 56 are preferably composed of a superelastic shape memory alloy, most preferably a nickel-titanium (nitinol) alloy which have been fixed in a curved shape by heat treatment as described for the flexible metal rod, above. As shown in FIG. 15, the flexible tubes 56 are disposed over the distal end portions of optical fibers 6 with distal ends of the fibers at or just proximal to the distal end of the tubes. The tubes 56 are open at both their distal and proximal ends to allow light to pass through the optical fibers and be emitted therefrom.

As described in the previous embodiments, the optical cable 4 is slidable within the sheath 12, so that the distal end portions of the fibers 6, and their attached metal tubes 56 can be retracted into and extended out of sheath 12, or sheath 12 can be retracted exposing metal tubes 56 and optical fibers 6 disposed therein. Tubes 56 become substantially straightened when confined within sheath 12, however, when the tubes 56 are extended out of the distal end of sheath 12, they resume their prefabricated curved memory-shape. The tubes can be arrayed in a linear, circular or any other desired configuration.

The distal ends 58 of tubes 56 can optionally be beveled in the form of a syringe needle to facilitate penetration of the tubes into tissue, for example, into the esophagus in the area of the sphincter or the tissue surrounding the female urethra below the bladder.

In the embodiments of the present invention in which the energy conducting cable 4 is a fiber optic cable, the free distal end portions of optical fibers 6 are preferably about 3 to about 25 millimeters long, most preferably about 6 to about 15 millimeters long. Optical fibers 6 preferably are made of quartz or fused silica, and have a core diameter of about 100 to about 600 microns, preferably about 200 to about 400 microns. As shown in FIG. 6, cable 4, comprising a plurality of optical fibers 6, is enclosed in a casing 34, which in this instance is a heat shrinkable film, such as polyethylene terephthalate (PET) or polytetrafluoroethylene (PTFE). Casing 34 can also be a sleeve made of PET, PTFE or any other flexible plastic material, as known in the art. The number of optical fibers contained in the cable 4 can vary from 1 to about 20, preferably from 1 to about 10.

Lasers which can be utilized with the above described devices include, without limitation argon, KTP, diode, Nd:YAG, Alexandrite and Holmium:YAG, the latter requiring optical fibers with a low hydroxyl or low-OH content. High intensity white light or filtered light of a desirable wavelength can also be used, as known in the art.

At a given position in close proximity to or in contact with the chordae tendineae, after the optical fibers have been deployed, an argon, KTP, diode, Nd:YAG, Alexandrite or other laser can be used to irradiate the tissue at an energy level of about 3 to about 30 watts for about one-half second to about 20 seconds, after which the device can be repositioned and the procedure repeated until a sufficient shrinkage or tightening of the chordae has occurred. A Holmium:YAG laser can be used, for example, by irradiating with a laser energy in the range of about 100 millijoules to about 500 millijoules per pulse at a repetition rate in the range of about 5 to 60 hertz, or at a laser energy in the range of about 500 millijoules to about 2 joules per pulse of laser energy at a repetition rate in the range of about 1 to about 30 hertz. The irradiation can be employed for a period of time in the range of about one-half second to about 20 seconds, after which the device can be repositioned and the procedure repeated.

The above described devices can be made of various elastic, flexible or rigid materials and in various sizes, depending upon the application. The outside diameter of sheath 12 is preferably in the range of about 1 millimeter to about 10 millimeters in diameter, more preferably in the range of about 2 to about 6 millimeters in diameter.

The energy conducting cable extends throughout the whole length of the device, generally exiting the device at the proximal end of the handpiece and extending further to a coupler at the proximal end of the cable, which is adapted for connection to an energy source. When the energy source is a laser generator, the coupler is an optical coupler, and the cable comprises at least one, and preferably several optical fibers.

Alternatively, the energy conducting cable can comprise one or more insulated wires, adapted at their proximal end for connection to an electrical power source. The distal ends of the wires, located in close proximity to the distal opening of the sheath, are adapted for connection to a variety of energy emitting devices, such as electrical resistive heating loops, ultrasonic or microwave generators, and RF electrodes. The individual wires are preferably bound together as described for the optical cable above. For example, the energy conducting cable 4 can comprise a pair of leads having a proximal end adapted for connection to an electrical power source and a distal end portion operably connected to an ultrasonic generator, such as a piezoelectric generator or a magnetostrictive generator. Alternatively, the distal end portion of the pair of leads can be operably connected to a resistive heating loop. Upon application of electric current through the leads, the energy from the ultrasonic generator or resistive heating loop heats nearby collagen-containing tissue and ultimately results in a shrinkage of that tissue.

In another embodiment, the energy conducting cable 4 comprises at least one insulted wire adapted at its proximal end for connection to a source of electric current, and having a distal end portion comprising a RF-electrode. Upon application of electric current to the RF-electrode, radio frequency energy is emitted from the electrode, which heats any nearby tissue, such as the chordae tendineae.

In use, as shown in FIGS. 4 and 5, an operator (not shown) positions the distal end of the sheath 12 within a ventricle of the heart, in close proximity to a papillary muscle, with both the distal end portion 24 of rod 18 and the distal end of cable 4 substantially retracted into sheath 12. The operator can guide the device into its desired position by a guide wire or can thread the device through a catheter that has been pre-positioned in the heart, or by any other acceptable method known in the coronary medical art. After proper positioning of the distal end of sheath 12 within a ventricle, near the chordae 28, the distal end portion 24 of the rod 18 is then slid forward to gradually extend the end portion of the rod from the opening at the distal end of the sheath. As the distal end portion 24 of the rod 18 becomes less constrained, it gradually resumes its prefabricated curved shape, and can thus encircle the papillary muscle 26 and then be manipulated up to encircle the chordae 28 that are attached to papillary muscle 26.

After rod 18 has encircled chordae 28, the operator extends the distal end of energy cable 4 out of the distal opening of sheath 12, placing the distal end of cable 4 in close proximity to or in contact with chordae 28. The curved end portion 24 of rod 18 acts as a stabilizer for the distal end of catheter 12. Thermal energy, in the form of coherent light (laser), high intensity non-coherent or filtered light, ultrasound, microwave or RF energy, or heat generated from an electrical resistive heating coil is supplied to the chordae, through the distal end of the energy cable 4, in a quantity sufficient to raise the temperature of the collagen in some or all of the chordae to about 50 to 55° C., causing the collagen strands to uncoil. The chordae strands shrink upon cooling of the collagen, thus tightening the cusps of the valve and preventing prolapse of the cusps into the atrium during the systole phase of the heart cycle. After the thermal irradiation of the chordae has ceased, the distal end portions of 18 and cable 4 can be withdrawn fully, or partially into the sheath 12, and the device can be repositioned for further treatment or removed entirely.

Figure 16:
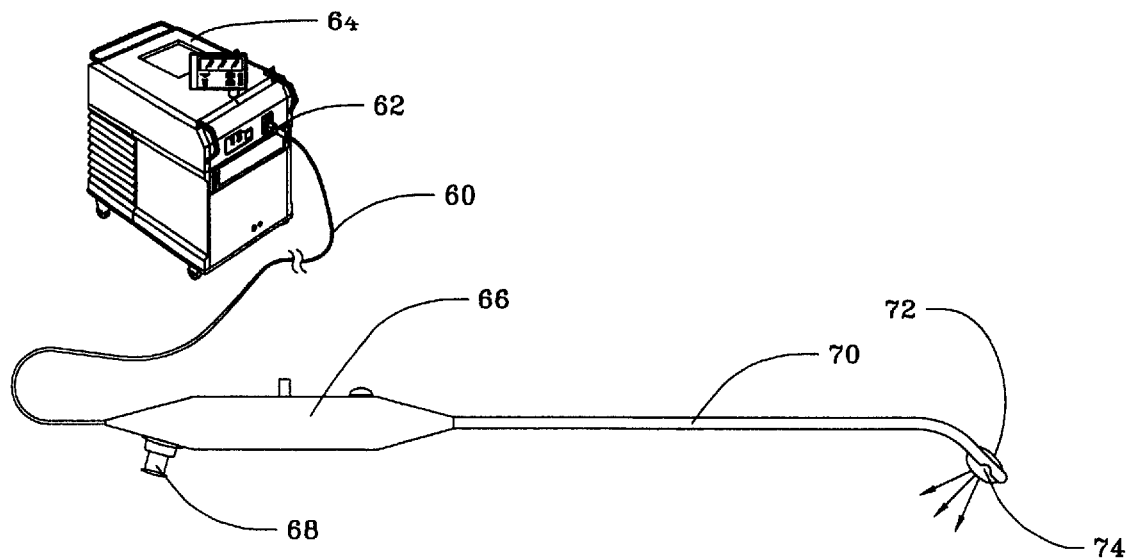
FIG. 16 is a schematic, external view of the elements of a preferred embodiment of the device of the present invention.

As shown in FIG. 16, a particularly preferred embodiment of the device of the present invention is comprised of optical fiber 60, which extends from a connector 62 that optically couples optical fiber 60 to a source of laser energy 64. Optical fiber 60 extends through and is fixably attached by an adhesive or the like to handpiece 66. Handpiece 66 contains a fluid port 68, such as a luer lock, to introduce a fluid into the hollow body of handpiece 66. Optical fiber 60 also extends through catheter 70, whose proximal end is fixably attached to the distal end of handpiece 66 by an adhesive or the like. Catheter 70 is in fluid communication with hollow handpiece 66 and balloon 72. Balloon 72 is fixably attached over the distal end portion of catheter 70, just proximal to its distal end. Emission port 74 enables laser energy to be emitted from catheter 70 through balloon 72, as shown by the arrows. The balloon 72 has an asymmetric shape, with the side of the balloon facing the emission port 74 being, when inflated, relatively greater in radius than the opposite side of balloon 72. Fluid can be pumped through handpiece 66 (not shown), catheter 70, and emission port 74 to inflate balloon 72 when it has been properly positioned for treatment. When balloon 72 is inflated with a radio or ultrasound-opaque fluid, the asymmetrical shape thereof enables the operator to ascertain the direction in which radiant energy will be emitted and to rotate and redirect the direction of emission.

Figure 17:
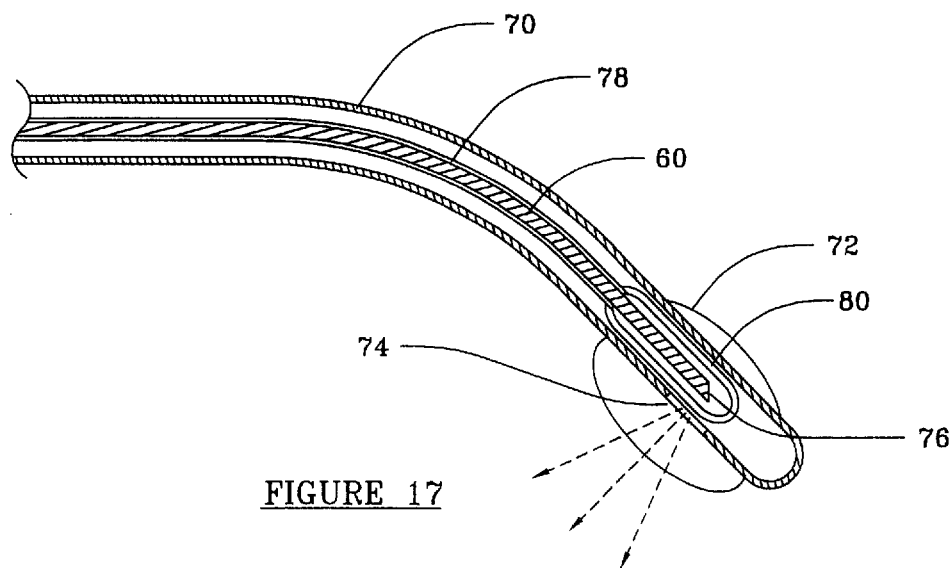
FIG. 17 is a partial, cross-sectional view of the distal end portion of an embodiment of the device of FIG. 16, which utilizes laser energy emitted at a right angle.

As shown in FIG. 17, the distal end of optical fiber 60 is beveled at an angle of approximately 39 degrees to obtain total internal reflection of the light energy, which exits emission port 74 and through balloon 72 laterally at an angle of about 60 degrees to about 100 degrees, preferably about 78 degrees, from the axis of optical fiber 60, as shown by the arrows. To provide an air environment, which is necessary to obtain total internal reflection of light energy, any vinyl cladding and buffer coat 78 are first removed from the exterior of the distal end portion of optical fiber 60, and then capillary tube 80 is fused to the glass cladding of the distal, bared end portion of optical fiber 60. Fusing of capillary tube 80 to optical fiber 60 can be accomplished, for example, by using a carbon dioxide laser, whose energy is absorbed by quartz or fused silica. Alternatively, capillary tube 80 can be affixed to the distal end portion of buffer coat 78 or to the glass cladding of optical fiber 60 by an adhesive or the like.

Figure 18:
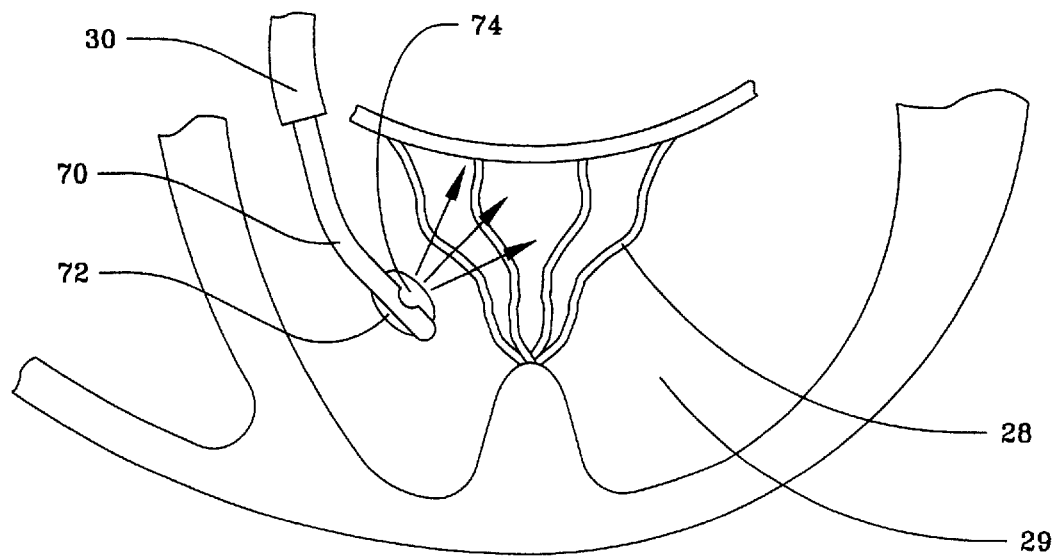
FIG. 18 is a partial, cross-sectional view of the left ventricle of a human heart and an exterior, partial view of the device of FIG. 16, positioned opposite the chordae tendineae.

As depicted in FIG. 18, the device of FIG. 16 has been advanced into the left ventricle 29 through a conventional guide catheter 30, such as made by Cook Vascular, Inc. of Leechburg, Pa., whose distal end portion can be permanently bent at a desired angle, such as 30 degrees, as shown. Any other angle can be used, from about 10 degrees to about 60 degrees, preferably about 20 degrees to about 50 degrees. The distal end portion of catheter 70 has likewise been formed into a permanently curved shape at an angle of about 10 degrees to about 60 degrees; preferably about 20 degrees to about 50 degrees.

By changing the relative positions of the bent distal end portion of guide catheter 30 and the bent distal end portion of catheter 70, the distal end of catheter 70 can be brought near to or into contact with the chordae tendineae 28, as well as near or into contact with the cusps or annulus of the valve. Laser energy, transmitted through optical fiber 60 (not shown) disposed within catheter 70, is directed by total internal reflection through emission port 74, and exits balloon 72, as shown by the arrows.

Figure 19:
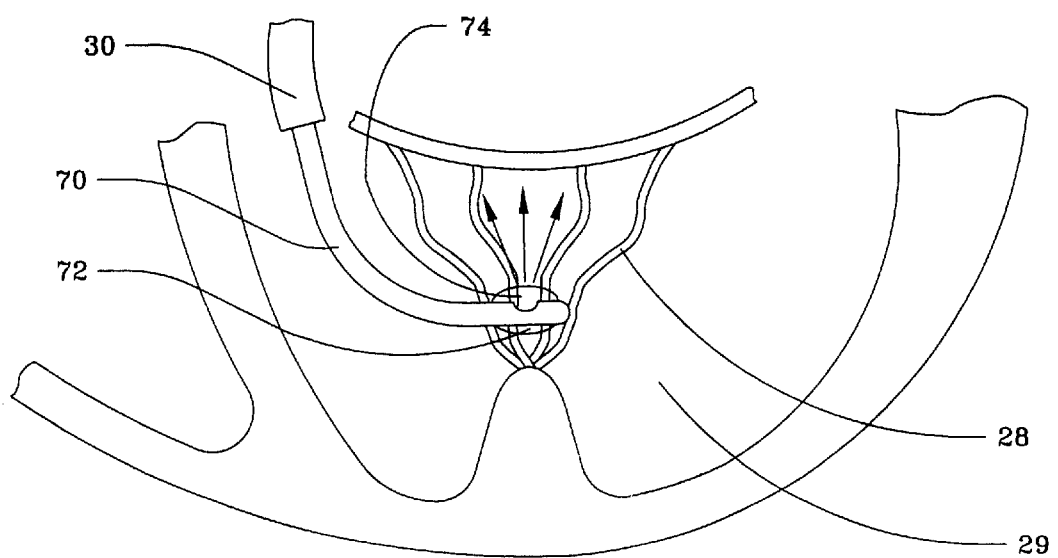
FIG. 19 is an exterior view of an embodiment of the device of FIG. 16, positioned opposite the chordae tendineae.

FIG. 19 illustrates an embodiment of the device of the present invention, in which the distal end portion of catheter 70 can be articulated at a desired angle, from 10 degrees to about 180 degrees, preferably from about 20 degrees to 170 degrees, from outside the body. In this embodiment, the device of FIG. 16 is introduced into left ventricle 29 through guide catheter 30, as known in the art. Catheter 70 is articulated, as shown, into an angle of about 90 degrees. Laser energy is emitted from emission port 74 and exits balloon 72, as shown by the arrows.

Figure 20:
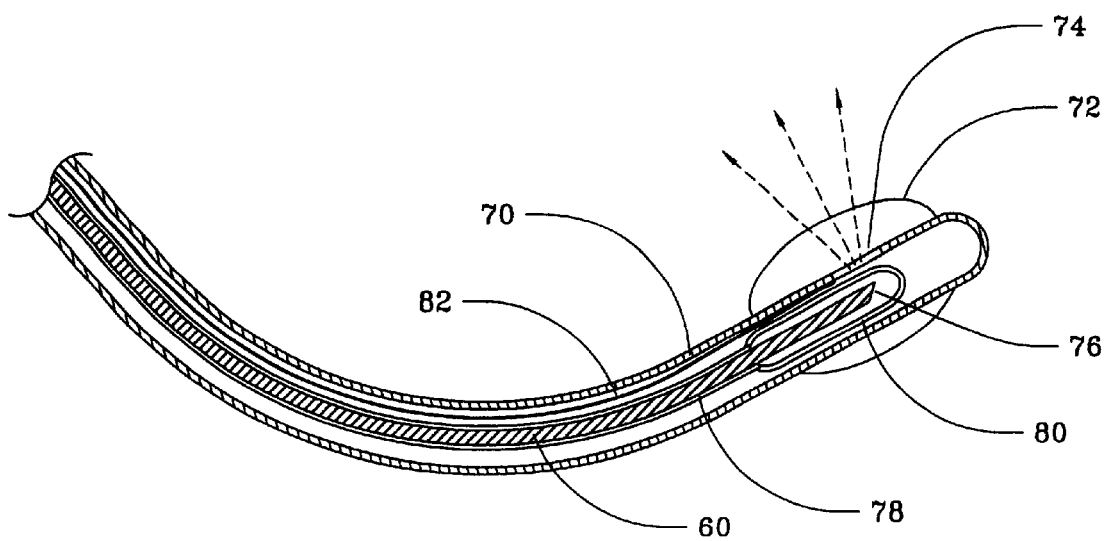
FIG. 20 is a partial cross-sectional view of the distal end portion of a preferred embodiment of the device of FIG. 16, having a control wire attached to the catheter wall to allow manipulation of the distal end of the catheter.

FIG. 20 illustrates the distal end portion of a preferred embodiment of the device of FIG. 16, in which articulation wire 82 is affixed to the interior surface of catheter 70 proximal to emission port 74. Articulation wire 82, when retracted, forces the distal end portion of catheter 70 into a desired angle. Again, in this embodiment, when balloon 72 is inflated and laser energy is transmitted through optical fiber 60, the laser energy exits emission port 74 and balloon 72 as shown by the arrows.

Figure 21:
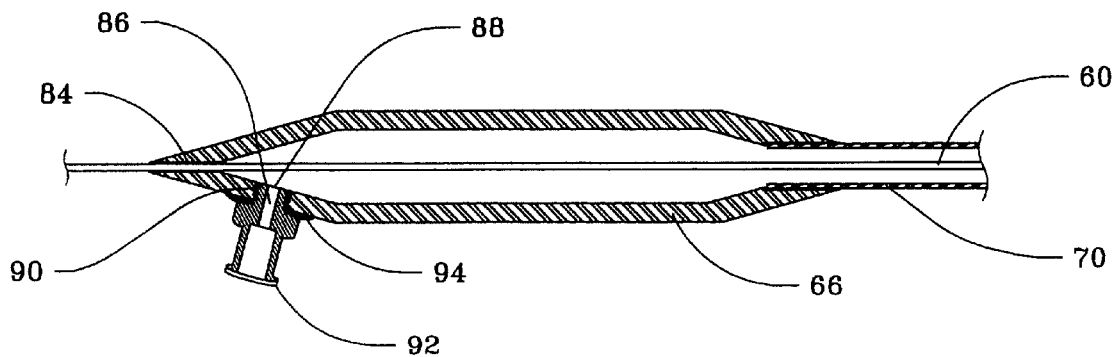
FIG. 21 is a cross-sectional view of an embodiment of the handpiece of the devices of FIGS. 16–20.

FIG. 21 illustrates details of handpiece 66 of the devices of FIGS. 16–20. Optical fiber 60 is fixedly attached to the proximal end of handpiece 66 by adhesive 84. Catheter 70 is affixed to the distal end of the handpiece 66 by an adhesive. The distal end of port 68 is affixed to a bore 88 in handpiece 66 by adhesive 90. Male luer lock 92 is affixed to the exterior surface of the proximal end of fluid port 68 by adhesive 94, as known in the art. Alternatively, a female luer lock can be employed, if desired.

Figure 22:
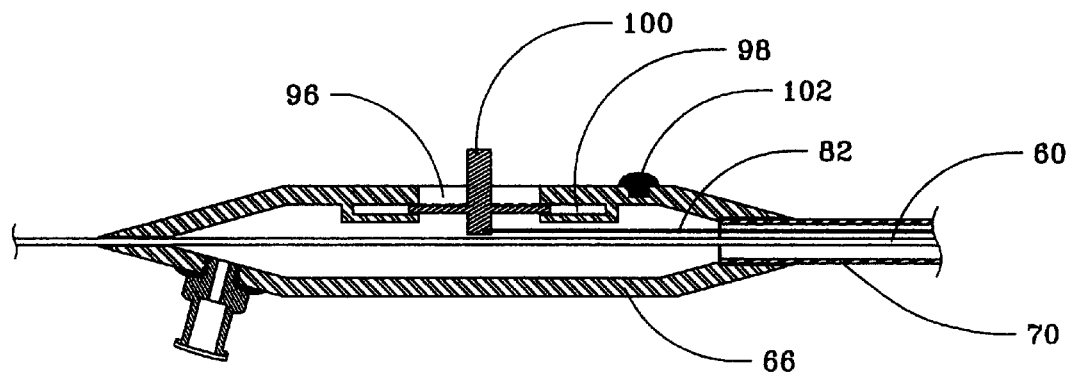
FIG. 22 is a cross-sectional view of an alternative embodiment of the handpiece of the device of FIGS. 16–20.

As seen in FIG. 22, handpiece 66 of the devices of FIGS. 16–20 contains channel 96 and track 98, within which lever 100 is slidably disposed. The proximal end of articulation wire 82 is affixed to lever 100. When lever 100 and attached wire 82 are retracted, the distal end portion of catheter 70 (as shown in FIGS. 19 and 20) is bent into a desired angle. Handpiece 66 contains button 102, which indicates to the user the direction in which laser energy will be emitted.

Figure 23:
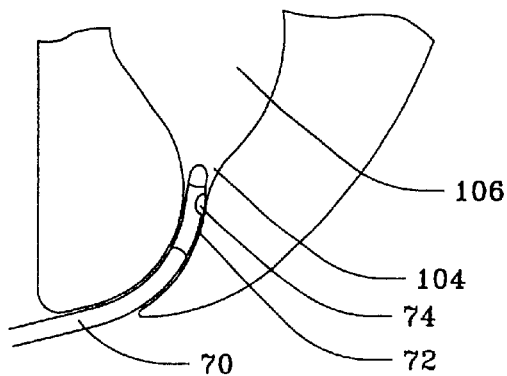
FIG. 23 is a partial, external view of the distal end portion of the devices of FIGS. 16–20 positioned in the female urethra below the bladder, with the balloon deflated.
Figure 24:
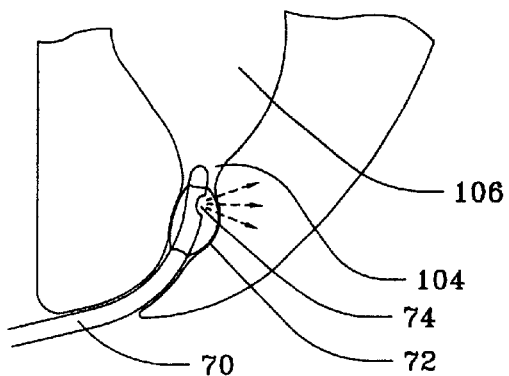
FIG. 24 is a partial, external view of the distal end portion of the device of FIGS. 16–20 positioned in the female urethra below the bladder, with the balloon inflated.

FIGS. 23 and 24 illustrate the devices of FIGS. 16–20 as they would be deployed in the female urethra below the bladder for the treatment of female stress incontinence (FSI).

As seen in FIG. 23, the distal end portion of catheter 70 is disposed within the female urethra 104 below the bladder 106, with balloon 72 deflated.

In FIG. 24, balloon 72 of the device of FIG. 23 has been inflated. Ultrasonic of X-ray imaging can be used to determine the orientation of the balloon, and thus the direction in which the laser energy will be emitted.

A cooling fluid, such as tap water, chilled water or saline, or a gas such as carbon dioxide, can be circulated through balloon 72 to inflate balloon 72 and cool the sensitive endothelial lining of urethra 104 in contact therewith. Cooling urethra 104 prevents damage to the urethral tissue by counteracting the thermal energy passing therethrough to heat and, ultimately, shrink the tissue underlying urethra 104.

Figure 25:
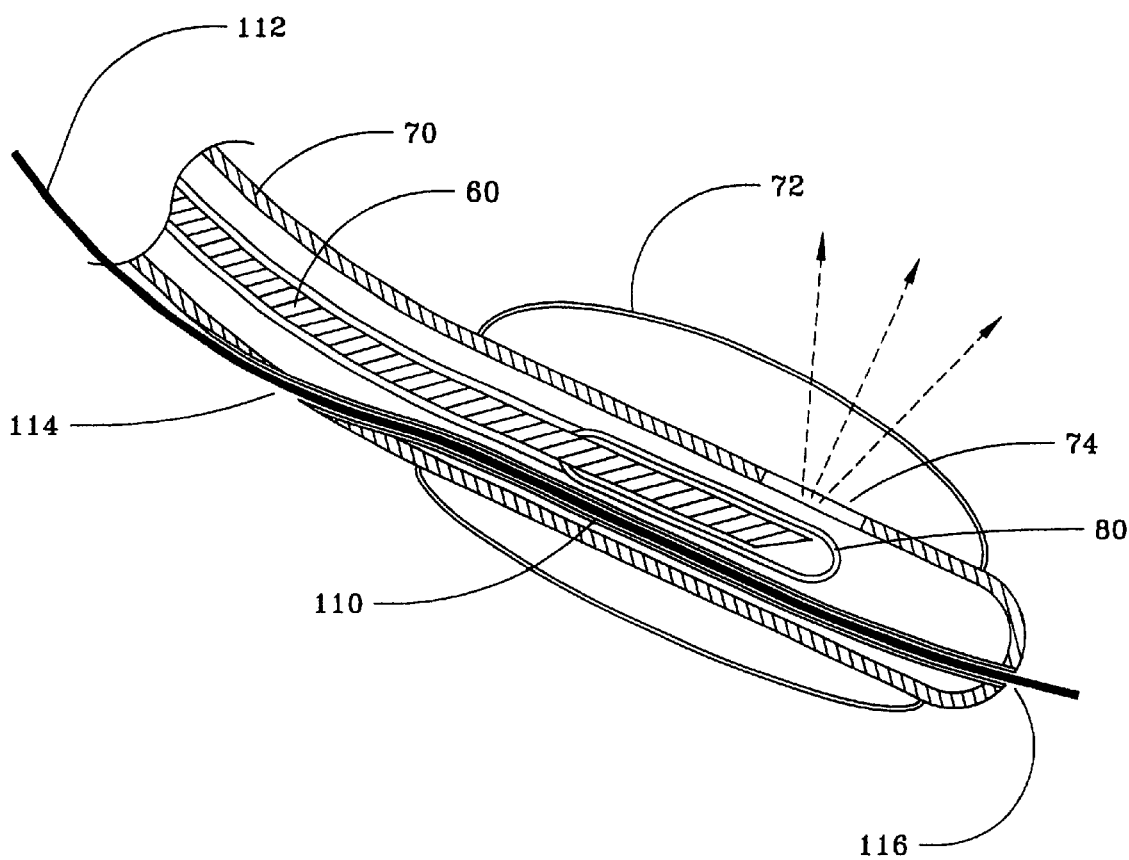
FIG. 25 is a partial, cross-sectional view of a preferred embodiment of the device of FIG. 16 which incorporates a channel for a guide wire.

As seen in FIG. 25, the devices of FIGS. 16–19 can also be inserted into the left ventricle by means of a guidewire. In this embodiment, cannula 110, which consists of a flexible plastic tube, preferably made of a thermally resistant plastic, such as a polyimide, is fixedly attached to catheter 70 at entry opening 114 in catheter 70, passes behind optical fiber 60 and the non-energy emitting side of capillary tube 80, and is fixedly attached to distal opening 116 of catheter 70. Thus, cannula 110 creates a passageway through the distal end portion of catheter 70, through which guidewire 112 can extend, as disclosed in co-owned U.S. Pat. No. 4,773,413 to Hussein et al., the relevant portions of which are incorporated herein by reference. Cannula 110 and guidewire 112 pass behind optical fiber 60 and capillary tube 80 to avoid being heated and damaged by laser energy emitted from the energy emitting surface of capillary tube 80 through laser energy emission port 74, as shown by the arrows. Likewise, cannula 110, creating a pathway for guidewire 112, can be incorporated in any of the devices described herein. Optionally, the distal end of catheter 70 can comprise an ultrasound—or radio opaque band to further aid in determining the position of catheter 70 within a patient's body.

Lasers which can be used in conjunction with optical fibers of the devices of the present invention include, but are not limited to, argon KTP, pulsed dye, diode, Nd:YAG, Alexandrite, Holmium:YAG and others. Of these, Holmium:YAG energy requires the use of low-OH optical fibers. Fluids that can be used to inflate the balloon of the devices of the present invention, for use with the sources of energy listed below, include, but are not limited to, the following: for a Holmium:YAG laser, a non-aqueous fluid, such as a perfluorocarbon, carbon dioxide or nitrogen gas can be utilized; for Argon, KTP, pulsed dye, diode, or Nd:YAG lasers, saline, an aqueous radio-opaque fluid, such as Hexabrix®, or an aqueous ultrasound-opaque fluid, such as Optison®, both available from Mallinckrodt, Inc. of St. Louis, Mo., carbon dioxide or nitrogen gas can be used.

Elastic, compliant materials that can be used for the balloon include, but are not limited to, latex and silicone. Plastic, non-complaint films that can be used for the balloon include, but are not limited to, polyurethane, polyethylene, polyisoprene, polyethylene terephthalate or PET, nylon and Teflon, as known in the art. Of these, silicone and polyethylene are preferred.

It can also be desirable to shrink the cusps or the annulus of an incompetent (loose) heart valve, using the devices of the present invention. In such application the device is positioned near or in contact with the cusps or within the annulus of the valve and thermal energy is applied thereto.

In shrinking the chordae tendineae, the cusps, or the annulus of a heart valve, it can be desirable to apply laser, electrical, RF, microwave, ultrasound or other energy when the chordae, cusps, or annulus are relaxed at an appropriate time during the cardiac cycle, during diastole, systole or such other time as can be desired.

Human chordae have a similar form and collagen content to that of the pig chordae. Pig hearts were utilized in the following examples as a model for a human heart.

EXAMPLE 1

Shortening of Stressed Chordae Tendineae of Pig Hearts by Application of Laser Energy Porcine (pig) chordae tendineae were placed under water at about 18° C. The length of the chordae were measured with the chordae under a stress of about 0.2 lb. Three pulses of Holmium:YAG laser energy were applied to the chordae over a period of one-half second at the energies described in Table 1, below. After irradiation, the lengths the chordae were again measured with the chordae not under stress. The percentage of shrinkage of the stressed chordae are provided in Table 1.

TABLE 1

Mean Shrinkage of Pig Heart Chordae Tendineae After Irradiation With Laser Energy, with the Chordae Tendineae Under Stress.

| Energy Delivered | Percentage Shrinkage |
|---|---|
| 200 mj/pulse × 3 pulses = 0.6 joules | 7% |
| 800 mj/pulse × 3 pulses = 2.4 joules | 11% |

EXAMPLE 2

Shortening of Relaxed Chordae Tendineae of Pig Hearts by Application of Laser Energy Porcine (pig) chordae tendineae were placed under water at 18° C. The length of the chordae were measured with the chordae relaxed. Three pulses of Holmium:YAG laser energy were applied to the chordae over a period of one-half second at the energies described in Table 2, below. After irradiation, the lengths the chordae were again measured with the chordae relaxed. The percentage of shrinkage of the relaxed chordae are provided in Table 2.

TABLE 2

Mean Shrinkage of Pig Heart Chordae Tendineae After Irradiation With Laser Energy, with the Chordae Tendineae Relaxed.

| Energy Delivered | Percentage Shrinkage |
|---|---|
| 200 mj/pulse × 3 pulses = 1.2 joules | 24% |
| 800 mj/pulse × 3 pulses = 4.8 joules | 31% |

As is demonstrated in Example 1, Table 1, shrinkage of pig heart chordae of about 7% to about 11% was effected by laser treatment when the chordae were under stress during irradiation. Similar shrinkage is expected for human chordae, since they have a similar collagen content to the chordae of the pig. In Example 2, laser treatment of pig heart chordae with the chordae relaxed resulted in shrinkage of between about 24% to 31%. as shown in Table 2. This greater shrinkage effect can be achieved in practice by synchronizing the emission of the laser energy with the patient's ECG so as to irradiate the chordae during diastole, as described in co-owned U.S. Pat. No. 4,488,975 to Shturman et al., the relevant portions of which are incorporated herein by reference.

In use, the AcuNav® ultrasound catheter (Accuson, Inc. of Mountain View, Calif.) can be employed in "image" mode to maneuver the energy emitting tip of the catheter near to or in contact with the chordae of the mitral valve. Then, before emission of thermal energy, the AcuNav® catheter can be employed in "color doppler" mode, and blood can be seen spurting from the mitral valve during the heart's compression as bright red against a blue/purple field. Energy can be emitted at one or a series of points along the chordae, until the spurting of blood through the valve ceases. If, after the emission of thermal energy, spurting of blood continues, the energy emitting tip of the catheter can be moved near or into contact with the cusps or annulus of the valve, and thermal energy can be applied thereto to shrink the same.

Numerous variations and modifications of the embodiments described above can be effected without departing from the spirit and scope of the novel features of the invention. It is to be understood that no limitation with respect to the specific apparatus illustrated herein is intended or should be inferred. It is, of course, intended to cover by the appended claims all such modifications as fall within the scope of the claims.

We claim:

1. A catheter device, suitable for shrinking collagen in a patient's body tissue, having a proximal end for connection to a thermal energy source, a tubular body portion, and a distal end adapted for delivering thermal energy to the tissue, which catheter device comprises:
   (a) a hollow catheter defining a first lumen, having a closed distal end and a distal end portion defining an aperture in the first lumen;
   (b) an optical fiber within the first lumen of the catheter having a proximal end adapted for attachment to a laser source and a distal end portion situated within the distal end portion of the catheter, opposite the aperture;
   (c) an inflatable balloon affixed over the distal end portion of the catheter and covering the aperture therein; and
   (d) a hollow, cylindrical handpiece, affixed to the proximal end of the catheter and in open communication with the first lumen, said handpiece defining a port for delivery of an inflation medium to the balloon through the first lumen and aperture;
   wherein the distal end portion of the optical fiber is adapted to emit laser energy through the aperture in the distal end portion of the catheter; and the balloon has an asymmetric shape when inflated, the portion of the balloon facing the aperture being larger in radius than the portion of the balloon on the side opposite to the side of the catheter facing the aperture, such that the laser energy is directionally emitted through a relatively larger portion of the balloon.

2. The catheter device of claim 1 wherein the distal end portion of the catheter further defines a guide lumen, adapted for acceptance of a guide wire, said guide lumen comprising a tube penetrating the cannula at points spaced proximally and distally to the balloon and extending through the catheter between said points behind the optical fiber.

3. The catheter device of claim 1 further comprising a control wire within the first lumen of the catheter, said control wire having a distal end and a proximal end, the distal end of the control wire being attached to an inner surface of the distal end portion of the catheter, said control wire being adapted to manipulate the position and orientation of the distal end portion of the catheter.

4. The catheter device of claim 3 wherein the handpiece comprises a lever within a channel, said lever being operably attached to the control wire, such that movement of the lever within the channel causes the distal end portion of the catheter to bend in response to said lever movement.

5. The catheter device of claim 1 wherein the catheter further comprises a second lumen, and
   (e) a flexible metal rod is slidably disposed within the second lumen, said rod having a permanently curved end portion and a blunt distal end.

6. The catheter device of claim 5 wherein the flexible metal rod comprises a superelastic shape memory alloy of nickel and titanium.

7. The catheter device of claim 1 further comprising a source of laser energy, operably coupled to the proximal end of the optical fiber.

8. A catheter device, suitable for shrinking the chordae tendineae of the human heart, having a proximal end for connection to a thermal energy source, a tubular body portion, and a distal end adapted for delivering thermal energy to the chordae tendineae, which catheter device comprises:
   (a) a tubular sheath defining at least a first lumen and a second lumen, each lumen having an opening at its distal end;
   (b) a fiber optic bundle, having a proximal end adapted for attachment to a source of laser energy, comprising a plurality of optical fibers, slidably disposed within the first lumen, each fiber having a distal end portion comprising a flexible curved metal tube, coaxially disposed over and affixed to the end portion of the fiber, such that the distal end of each fiber terminates just proximal to the distal end of the tube; and
   (c) a flexible metal rod having a permanently curved end portion and a blunt distal end, slidably disposed within the second lumen of the sheath.

9. The catheter device of claim 8 wherein the optical fibers have core diameters in the range of about 100 microns to about 600 microns.

10. The catheter device of claim 8 wherein the distal end of each tube is beveled in the shape of a syringe needle, the beveled end being capable of penetrating a tissue into which it is extended.

11. The catheter device of claim 8 further comprising a source of laser energy operably coupled to the proximal end of the fiber optic bundle.

12. A catheter device, suitable for shrinking collagen in a patient's body tissue, having a proximal end for connection to a thermal energy source, a tubular body portion, and a distal end adapted for delivering thermal energy to the tissue, which catheter device comprises:
   (a) a hollow catheter defining a first lumen, having a closed distal end and a distal end portion defining an aperture in the first lumen;
   (b) an optical fiber within the first lumen of the catheter having a proximal end adapted for attachment to a laser source and a distal end portion situated within the distal end portion of the catheter, opposite the aperture;

(c) an inflatable balloon affixed over the distal end portion of the catheter and covering the aperture therein; and (d) a hollow, cylindrical handpiece, affixed to the proximal end of the catheter and in open communication with the first lumen, said handpiece defining a port for delivery of an inflation medium to the balloon through the first lumen and aperture;

wherein the distal end portion of the optical fiber is adapted to emit laser energy through the aperture in the distal end portion of the catheter and the distal end of the optical fiber is beveled at an angle of about 39 degrees and the distal end portion of the optical fiber is sealed within a glass capillary tube, such that laser energy is emitted at an angle of about 60 to about 100 degrees from the axis of the distal end portion of the fiber when the optical fiber is attached to a laser energy source; the balloon having an asymmetric shape when inflated, the portion of the balloon facing the aperture being larger in radius than the portion of the balloon on the side opposite to the side of the catheter facing the aperture, such that the laser energy is directionally emitted through a relatively larger portion of the balloon.

13. A catheter device, suitable for shrinking collagen in a patient's body tissue, having a proximal end for connection to a thermal energy source, a tubular body portion, and a distal end adapted for delivering thermal energy to the tissue, which catheter device comprises:

(a) a hollow catheter defining a first lumen, having a closed distal end and a distal end portion defining an aperture in the first lumen;

(b) an optical fiber within the first lumen of the catheter having a proximal end adapted for attachment to a laser source and a distal end portion situated within the distal end portion of the catheter, opposite the aperture;

(c) an inflatable balloon affixed over the distal end portion of the catheter and covering the aperture therein;

(d) a hollow, cylindrical handpiece, affixed to the proximal end of the catheter and in open communication with the first lumen, said handpiece defining a port for delivery of an inflation medium to the balloon through the first lumen and aperture; and (e) a control wire within the first lumen of the catheter, said control wire having a distal end and a proximal end, the distal end of the control wire being attached to an inner surface of the distal end portion of the catheter, said control wire being adapted to manipulate the position and orientation of the distal end portion of the catheter, the handpiece containing a reel mechanism comprising a shaft and a knob that is fixedly attached to one end of the shaft, wherein said shaft is pivotally moveable within said handpiece, said shaft being operably attached to the control wire, such that turning the knob causes the distal end portion of the catheter to bend in response to the turning of the knob;

wherein the distal end portion of the optical fiber is adapted to emit laser energy through the aperture in the distal end portion of the catheter; and the balloon has an asymmetric shape when inflated, the portion of the balloon facing the aperture being larger in radius than the portion of the balloon on the side opposite to the side of the catheter facing the aperture, such that the laser energy is directionally emitted through a relatively larger portion of the balloon.

14. A catheter device, suitable for shrinking collagen in a patient's body tissue, having a proximal end for connection to a thermal energy source, a tubular body portion, and a distal end adapted for delivering thermal energy to the tissue, which catheter device comprises:

(a) a hollow catheter defining a first lumen, having a closed distal end and a distal end portion defining an aperture in the first lumen;

(b) an optical fiber within the first lumen of the catheter having a proximal end adapted for attachment to a laser source and a distal end portion situated within the distal end portion of the catheter, opposite the aperture;

(c) an inflatable balloon affixed over the distal end portion of the catheter and covering the aperture therein;

(d) at least one thermocouple positioned at the distal end portion of the catheter, within the balloon, or on the surface of the balloon, adapted for measuring the temperature of the inflation medium in the balloon or the temperature at the surface of the balloon, respectively; and (e) a hollow, cylindrical handpiece, affixed to the proximal end of the catheter and in open communication with the first lumen, said handpiece defining a port for delivery of an inflation medium to the balloon through the first lumen and aperture;

wherein the distal end portion of the optical fiber is adapted to emit laser energy through the aperture in the distal end portion of the catheter; and the balloon has an asymmetric shape when inflated, the portion of the balloon facing the aperture being larger in radius than the portion of the balloon on the side opposite to the side of the catheter facing the aperture, such that the laser energy is directionally emitted through a relatively larger portion of the balloon.

15. A catheter device, suitable for shrinking collagen in a patient's body tissue, having a proximal end for connection to a thermal energy source, a tubular body portion, and a distal end adapted for delivering thermal energy to the tissue, which catheter device comprises:

(a) a hollow catheter defining a first lumen, having a closed distal end and a distal end portion defining an aperture in the first lumen;

(b) an optical fiber within the first lumen of the catheter having a proximal end adapted for attachment to a laser source and a distal end portion situated within the distal end portion of the catheter, opposite the aperture;

(c) an inflatable balloon affixed over the distal end portion of the catheter and covering the aperture therein; and (d) a hollow, cylindrical handpiece, affixed to the proximal end of the catheter and in open communication with the first lumen, said handpiece defining a port for delivery of an inflation medium to the balloon through the first lumen and aperture, the inflation medium comprising a cooling fluid, capable of cooling a tissue in contact with the balloon;

wherein the distal end portion of the optical fiber is adapted to emit laser energy through the aperture in the distal end portion of the catheter; and the balloon has an asymmetric shape when inflated, the portion of the balloon facing the aperture being larger in radius than the portion of the balloon on the side opposite to the side of the catheter facing the aperture, such that the laser energy is directionally emitted through a relatively larger portion of the balloon.

16. A catheter device, suitable for shrinking the chordae tendineae of the human heart, having a proximal end for connection to a thermal energy source, a tubular body portion, and a distal end adapted for delivering thermal energy to the chordae tendineae, which catheter device comprises:

(a) a tubular sheath having an opening at its distal end;

(b) an energy conducting cable, slidably disposed within the sheath, having a proximal end adapted for attachment to an energy source and a distal end portion adapted for delivering thermal energy to a predetermined region of the chordae tendineae and at least one terminal in the distal end portion comprising a radio frequency electrode; and (c) a flexible metal rod slidably disposed within the sheath having a permanently curved end portion and a blunt distal end.

17. A catheter device, suitable for shrinking the chordae tendineae of the human heart, having a proximal end for connection to a thermal energy source, a tubular body portion, and a distal end adapted for delivering thermal energy to the chordae tendineae, which catheter device comprises:

(a) a tubular sheath having an opening at its distal end;

(b) an energy conducting cable, slidably disposed within the sheath, having a proximal end adapted for attachment to an energy source, a distal end portion adapted for delivering thermal energy to a predetermined region of the chordae tendineae and a pair of leads having a proximal end adapted for connection to an electrical power source and a distal end portion operably connected to a resistive heating loop; and (c) a flexible metal rod slidably disposed within the sheath, having a permanently curved end portion and a blunt distal end.

* * * * *